(12) United States Patent
Ishii

(10) Patent No.: US 7,163,524 B2
(45) Date of Patent: Jan. 16, 2007

(54) CATHETER

(75) Inventor: Tatsuzo Ishii, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/368,432

(22) Filed: Feb. 20, 2003

(65) Prior Publication Data

US 2003/0163117 A1   Aug. 28, 2003

(30) Foreign Application Priority Data

Feb. 27, 2002   (JP) ............. 2002-052086
Feb. 27, 2002   (JP) ............. 2002-052087

(51) Int. Cl.
*A61M 29/00* (2006.01)
*A61M 31/00* (2006.01)
*A61M 37/00* (2006.01)

(52) U.S. Cl. .............. 604/103.04; 604/96.01

(58) Field of Classification Search ............ 604/96.01, 604/103.4, 523, 534, 103.04
See application file for complete search history.

(56) References Cited

U.S. PATENT DOCUMENTS 4,943,278 A * 7/1990 Euteneuer et al. .......... 606/194

5,156,594 A   10/1992 Keith
5,947,925 A   9/1999 Ashiya et al.
6,503,223 B1 * 1/2003 Sekido et al. ............ 604/96.01

FOREIGN PATENT DOCUMENTS

| EP | 0 397 357 | 11/1990 |
|---|---|---|
| EP | 0 796 633 A1 | 9/1997 |
| JP | 4-9548 B2 | 2/1992 |
| JP | 8-308933 A | 11/1996 |
| JP | 9-271517 A | 10/1997 |
| WO | WO 01/93941 A1 | 12/2001 |

OTHER PUBLICATIONS

Corresponds to EP 0 397 357.

* cited by examiner

*Primary Examiner*—Kevin C. Sirmons
*Assistant Examiner*—Bhisma Mehta
(74) *Attorney, Agent, or Firm*—Buchanan Ingersoll & Rooney PC

(57) ABSTRACT

The catheter 1 of the present invention has a tubular catheter body 2 made from a metal material. A groove 21 is formed in the outer periphery of the catheter body 2 in the longitudinal direction. This groove 21 is formed by plastically transforming the tubular wall of the catheter body 2 by plastic treatment. Thus, there is provided a catheter which has excellent followability and high ease of operation while maintaining torque transmissibility and pushability.

1 Claim, 11 Drawing Sheets

CATHETER

BACKGROUND OF THE INVENTION

1. Field of the Invention

The present invention relates to a catheter to be inserted into a body lumen, vessel or duct such as a blood vessel for use. The present invention also relates to a balloon catheter having a balloon in the distal end portion thereof, and particularly, to a rapid-exchange type balloon catheter.

2. Description of the Related Art

In recent years, intravascular operations have been widely performed to treat a lesion part of a blood vessel by inserting a catheter into the blood vessel percutaneously without carrying out a surgical operation. In these operations, a catheter must be selectively inserted into an intricately bending, meandering or branching narrow blood vessel to position its distal end portion at the targeted site.

In general, in order to insert a catheter into the blood vessel percutaneously, the catheter is made to reach the targeted site while a guide wire (introduction aid tool) is inserted into the lumen of the catheter. On this occasion, generally, the catheter is preceded by a guide wire and advanced to the target site in the blood vessel.

To guide the catheter having the guide wire inserted therein into the targeted site of the body, the operation of moving forward or backward or turning the guide wire and the catheter is carried out from an end side in vitro thereof. This operation must be transmitted to the distal end side of the catheter without fail. Therefore, torque transmissibility and pushability are required for the catheter.

When the body portion (catheter body) of a relatively thin catheter having a small diameter to be applied to a narrow blood vessel is made from a synthetic resin material, it may have low stiffness or be readily kinked, whereby the above-mentioned torque transmissibility and pushability may not be obtained fully. Therefore, the catheter body of the relatively narrow catheter is made of a metal tube having bending elasticity.

However, when the catheter body is made of a metal tube, the distal end side portion of the catheter body especially has too high flexural rigidity and lacks flexibility. Therefore, it is inferior in follow-up ability (followability) which enables it to follow the preceding guide wire in the winding blood vessel smoothly and reliably.

A balloon catheter to be inserted into the blood vessel typified by a catheter used for PTCA (Percutaneous Transluminal Coronary Angioplasty) (to be referred to as "PTCA catheter" hereinafter) has a guide wire lumen for inserting a guide wire which is formed along the entire length of the catheter in addition to a balloon lumen for inflating the balloon. Prior to the insertion of the catheter into the blood vessel, the guide wire is inserted into the guide wire lumen and the distal end portion of the guide wire is guided to the targeted site (near a stricture in the blood vessel) together with the catheter in such a manner that the distal end of the guide wire precedes the catheter.

There are many variations of the PTCA catheter which differ in the size of a balloon to be suited to a case of a disease such as the size of the stricture site and the diameter of the blood vessel or to expand the stricture site stepwise. After insertion into the blood vessel, the work of exchanging the PTCA catheter may be necessary. Even when a plurality of indwelling units for securing an inner diameter in the blood vessel, called "stent", are installed, the catheter may be removed from and inserted into the blood vessel several times.

The exchange of the catheter described above is preferably carried out while the guide wire is left in the blood vessel to reduce a burden on a patient, the operation time and the labor, to prevent infection, or the like.

However, since the guide wire lumen is formed along the entire length of the conventional catheter as described above, in order to exchange the catheter from the in-vitro end side (proximal end side) of the guide wire while the guide wire is left in the blood vessel, the in-vitro end of the guide wire must be projected from the proximal end of the catheter to a length longer than the total length of the catheter. That is, the length of the guide wire must be twice or more the length of the catheter and there is a problem that such long projecting guide wire reduces ease of the operation.

There is proposed a rapid-exchange type catheter having a guide wire lumen formed only in the distal end portion of the catheter, that is, a catheter in which an opening at the distal end of the catheter communicates with a side hole formed at a position several centimeters away from the opening toward the proximal end and this short lumen is engaged with a guide wire (EP 0397357 A1 (JP 4-9548 B)). This catheter can be exchanged while the guide wire is left in the blood vessel without projecting the in-vitro end of the guide wire long from the proximal end of the catheter.

In order to guide the catheter to the targeted site in vivo while the guide wire is inserted in the guide wire lumen, as the blood vessel meanders, the guide wire and the catheter must conform to the curvature of the meandering blood vessel. In order to conform to this curvature, the operation of moving forward or backward or turning the guide wire and the catheter is carried out on the in-vitro end side. This operation must be transmitted to the distal end side of the catheter without fail. To this end, torque transmissibility, pushability and kink resistance are required for the catheter.

When the body portion (catheter body) of a relatively small catheter to be applied to a narrow blood vessel is made from a synthetic resin material, it may have low stiffness and be readily kinked, whereby the above-mentioned torque transmissibility and pushability may not be obtained fully. Therefore, the catheter body of the relatively small catheter is made of a metal tube having bending elasticity.

However, when the catheter body is made of a metal tube, the distal end side portion of the catheter body especially has too high flexural rigidity and lacks flexibility. Therefore, it is inferior in follow-up ability (followability) which enables it to follow the preceding guide wire in the winding blood vessel smoothly and reliably.

SUMMARY OF THE INVENTION

It is an object of the present invention to provide a catheter, balloon catheter or rapid-exchange type catheter which easily winds in a specific direction and has excellent followability and high ease of operation while securing torque transmissibility and pushability.

This object is attained by the present invention described as (1) to (11) in the following.

(1) A catheter having a tubular catheter body made from a metal material, in which:

the catheter body has a groove formed in a longitudinal direction in the outer periphery of at least the distal end side portion thereof in such a manner that the tubular wall is caved in; and the thickness of the tubular wall of the catheter body is almost constant along the entire circumference including the groove formed portion.

(2) A balloon catheter including:

a tubular catheter body made from a metal material;

a balloon which can be inflated and deflated and is mounted on the distal end side of the catheter body;

a balloon lumen which is formed of the lumen of the catheter body and that communicates with the inside of the balloon; and a guide wire lumen which is open to the distal end side of the balloon, is surrounded by the tubular wall in the balloon and has a guide wire inserted from the distal end side of the balloon to the outside of the catheter body therein, in which:

the catheter body has a groove formed in a longitudinal direction in the outer periphery of at least the distal end side portion thereof in such a manner that the tubular wall is caved in; and the thickness of the tubular wall of the catheter body is almost constant along the entire circumference including the groove formed portion.

(3) A catheter or balloon catheter according to the item (1) or (2) described above, in which the groove is formed along almost the entire length of the catheter body.

(4) A catheter or balloon catheter according to any one of the items (1) to (3) described above which has a portion where the depth of the groove decreases continuously or stepwise toward the proximal end.

(5) A balloon catheter according to any one of the items (2) to (4) described above, in which at least the part of the guide wire can be inserted into the groove.

(6) A balloon catheter according to any one of the items (2) to (5) described above, in which an opening at the proximal end of the guide wire lumen is formed continuous to the distal end portion of the groove.

(7) A balloon catheter according to any one of the items (2) to (6) described above, in which an inner tube is inserted into the balloon and the guide wire lumen is formed of the lumen of the inner tube.

(8) A catheter or balloon catheter according to any one of the items (1) to (7) described above, in which the catheter body is made from stainless steel or pseudoelastic alloy.

(9) A catheter or balloon catheter according to any one of the items (1) to (8) described above which further has a tubular member, made from a synthetic resin material, for covering the outer periphery of at least the distal end side portion of the catheter body and extending farther in the distal end direction than the distal end of the catheter body.

(10) A catheter or balloon catheter according to any one of the items (1) to (9) described above, in which plural slits are formed in the tubular wall of the distal end side portion of the catheter body and extend in a direction almost perpendicular to the longitudinal direction of the catheter body.

(11) A catheter or balloon catheter according to any one of the items (1) to (10) described above, in which spiral slits are formed in the tubular wall of the distal end side portion of the catheter body and in which the spiral pitch between the spiral slits become smaller continuously or stepwise toward the distal end.

DETAILED DESCRIPTION OF THE INVENTION

A catheter of the present invention will be described in detail hereinafter based on preferred embodiments shown in the accompanying drawings.

Embodiment 1

Figure 1:
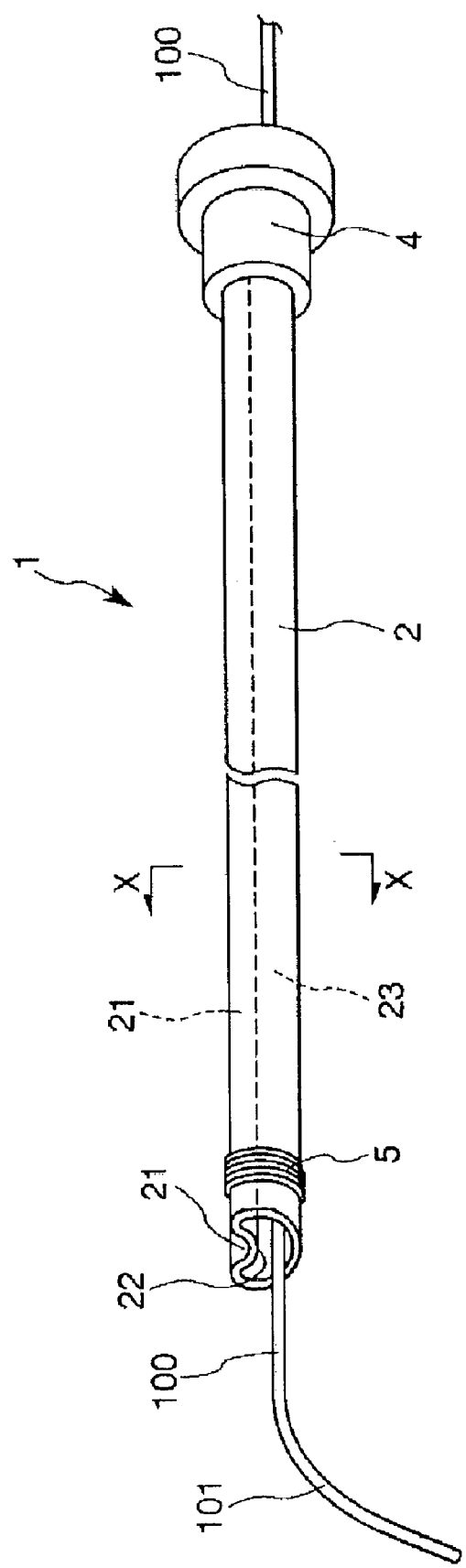
FIG. 1 is a perspective view of Embodiment 1 of a catheter of the present invention (guide wire is inserted into a lumen)
Figure 2:
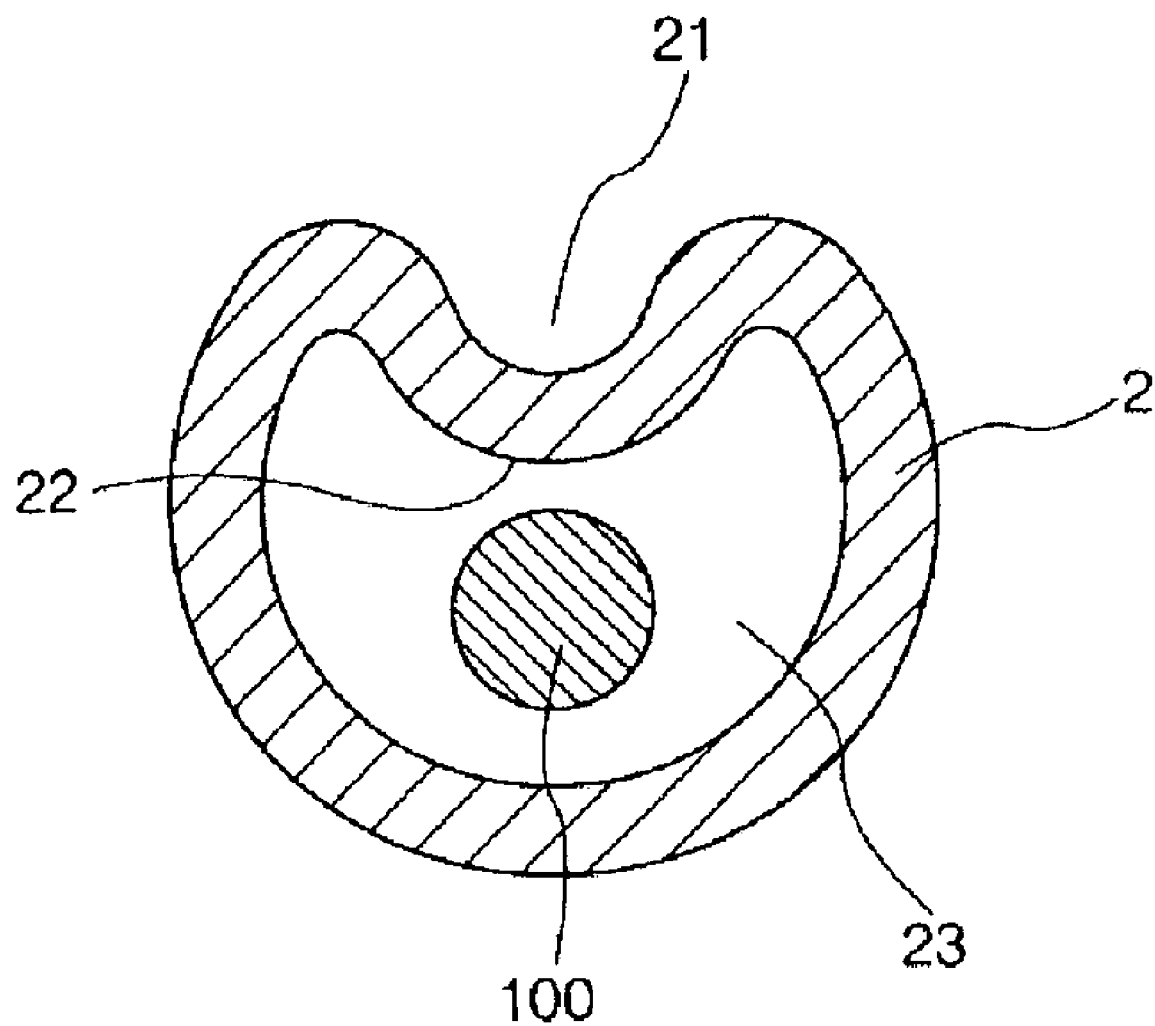
FIG. 2 is a sectional view (transverse sectional view) taken along the line X—X of FIG. 1.
Figure 3:
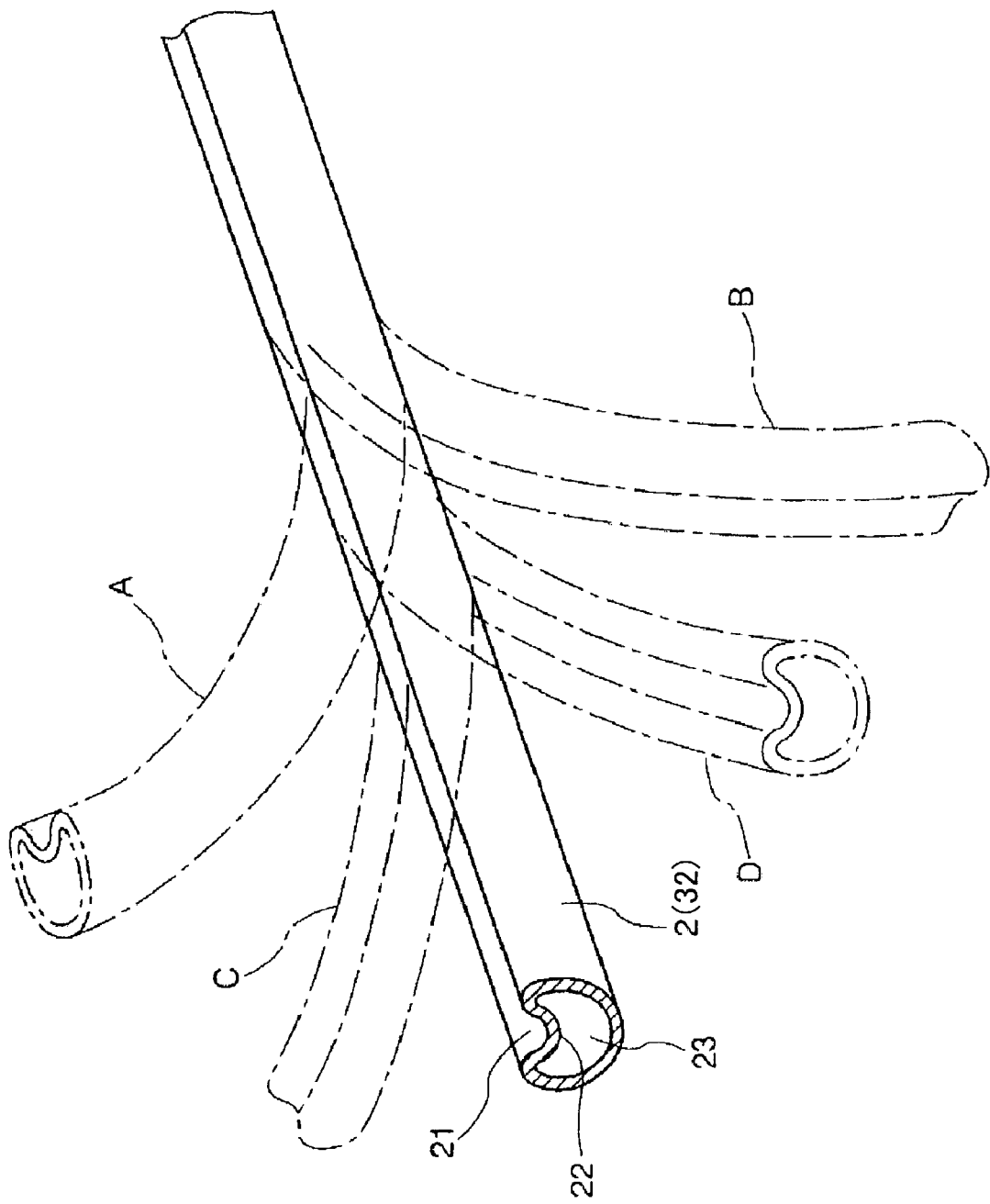
FIG. 3 is a perspective view of a catheter body of the catheter shown in FIG. 1.

FIG. 1 is a perspective view of Embodiment 1 of a catheter of the present invention (a guide wire is inserted into a lumen of the catheter), FIG. 2 is a sectional view taken along the line X—X of FIG. 1 (transverse sectional view), and FIG. 3 is a perspective view of a catheter body of the catheter shown in FIG. 1. In the following description, the right side (side close at hand of the operation of inserting into the body) of each figure is referred to as "proximal end" and the left side (distal end side to be inserted into the body) is referred to as "distal end".

The catheter 1 shown in FIG. 1 includes a small and long catheter body 2 having bending elasticity and a hub 4 mounted to the proximal end of the catheter body 2. The constitution of each element of the catheter will be described hereinafter.

The catheter body 2 is inserted into a body lumen, vessel or duct such as a blood vessel (to be typified by a blood vessel hereinafter) and is tubular. A tubular lumen (lumen) 23 is formed in the catheter body 2 from the distal end to the proximal end thereof. When the catheter body 2 is to be inserted into the blood vessel, a guide wire 100 to be described below is inserted into the tubular lumen 23. The tubular lumen 23 is also used as the passage of a liquid such as physiological saline, medical fluid, cleaning fluid, contrast medium or body fluid (such as blood).

This catheter body 2 is made from a metal material. Thus, the catheter body 2 has higher rigidity (flexural rigidity and torsional rigidity) than a catheter body made from a synthetic resin material (plastic). Therefore, the catheter body 2 has high stiffness even when its outer diameter is relatively small. As a result, the catheter 1 becomes excellent in torque transmissibility that torque applied from the proximal end can be transmitted to the distal end without fail and in pushability that an operator's push-in force for advancing the catheter in the blood vessel can be transmitted to the distal end side from the proximal end side without fail. It also becomes excellent in kink resistance.

That is, the catheter 1 of the present invention has high ease of operation even when the outer diameter of the catheter body 2 is relatively small, whereby it can be preferably inserted into a relatively narrow blood vessel, in particular. The outer diameter (average outer diameter) of the catheter body 2 is not particularly limited but preferably about 0.2 to 5 mm, more preferably about 0.3 to 3 mm. The inner and outer diameters of the catheter body 2 may change in the longitudinal direction.

The length of the catheter body 2 is not particularly limited and is suitably determined according to the use site of the catheter 1 and a case of a disease but generally, it is preferably about 80 to 200 cm.

The structural material of the catheter body 2 may be a metal material but preferably a pseudoelastic alloy (super elastic alloy) such as Ni—Ti alloy or stainless steel from the viewpoints of physical properties and safety. That is, the pseudoelastic alloy or stainless steel is readily returned to its original form by the removal of stress. The pseudoelastic alloy includes what is obtained by hot processing or cold processing, what is obtained by both hot processing and cold processing, and further what is obtained by another processing if it returns to its original form after transformation. Therefore, it includes what has almost constant stress even when distortion increases and what has increasing distortion as stress grows in a stress-distortion curve.

As shown in FIG. 1 and FIG. 2, a single groove (depression) 21 is formed in the outer periphery (side surface) of the catheter body 2 in the longitudinal direction (axial direction) of the catheter body 2 in such a manner that the tubular wall is caved in.

The sectional form of the groove 21 is almost arcuate in this embodiment. The sectional form is not limited to this and may be V-shaped, U-shaped, rectangular, oval (semi-oval), or the like.

The groove 21 is formed by plastically processing the tubular wall of the catheter body 2 having a circular section to plastically transform it. This plastic processing can be easily carried out by the following methods, for instance. (1) The method of which the unprocessed catheter body 2 is inserted into a flask having a semi-circular section and an inner periphery with the same curvature as that of the outer periphery (side surface) of the catheter body 2, a jig (such as a pin) having a projection corresponding to the groove 21 is installed at a position opposite to the flask, and the catheter body 2 is moved relative to the flask and the jig so that it is pulled out in the longitudinal direction (axial direction) from between the flask and the jig while the jig is applied to the catheter body 2 to form the groove 21 in the longitudinal direction gradually. (2) The method of which a mile mold having a projecting rib corresponding to the groove 21 is pressed against the outer periphery of the catheter body 2 supported in a flask and the groove 21 equal to the length of the projecting rib is formed in one operation.

Since the tubular wall of a portion which has been pressed by the projection of the above-mentioned jig or the projecting rib of the above-mentioned male mold in the plastic processing escapes toward the lumen side of the catheter body 2 to form a projection 22, the thickness of the tubular wall of the catheter body 2 is almost constant along the entire circumference of the tube including the groove 21 formed portion. As a result, the strength of the groove 21 formed portion is not reduced and even when the thickness of the tubular wall of the catheter body 2 is relatively small, the deformation, damage, or the like of the groove 21 formed portion can be effectively prevented.

Further, when the catheter body 2 is made from a pseudoelastic alloy, the groove 21 may be formed simultaneously with cold processing or hot processing or before or after cold processing or hot processing.

Since the above-mentioned groove 21 is formed in the catheter body 2, it has a property (characteristic) that its flexural rigidity differs according to its bending direction. That is, when the catheter body 2 is bent upward so that the groove 21 formed portion is located on the inner side (state shown by A in FIG. 3), the flexural rigidity of the catheter body 2 is lower than that when it is bent downward so that the groove 21 formed portion is located on the outer side (state shown by B in FIG. 3) or when it is bent sideways so that a portion 90° away from the groove 21 formed portion is positioned on the inner side (or outer side) (state shown by C and D in FIG. 3). Thus, the catheter body 2 of the groove 21 formed portion is selectively readily bent in the direction shown by A in FIG. 3.

As the catheter body 2 of the catheter 1 has the above-mentioned property, it has excellent follow-up ability (to be referred to as "followability" hereinafter) so that it can be inserted along the preceding guide wire 100 in the winding blood vessel smoothly and reliably. This is because when the catheter body 2 is to be inserted and advanced along the preceding guide wire 100, the catheter 1 is turned such that the groove 21 formed portion is positioned on the inner side of curvature in conformity to the curvature of the intricately branching and winding blood vessel, whereby the catheter body 2 is readily bent in accordance with the curvature of the blood vessel and thus can be inserted and advanced smoothly and reliably.

Thus, the catheter 1 exhibits excellent followability. Further, as described above, the catheter body 2 of the catheter 1 has high stiffness with relatively high rigidity so that the catheter 1 has excellent torque transmissibility and pushability. That is, the catheter 1 of the present invention has excellent torque transmissibility and pushability as well as excellent followability. Thus, it has extremely high ease of operation.

The inventor of the present invention conducted the following three-point bending test on a metal tube to prove that the flexural rigidity of the catheter body 2 is changed according to its bending direction by the formation of the groove 21 as described above. In this 3-point bending test, the amount of deflection was measured when the metal tube was bent at 3 points under the following conditions.

<Metal Tube> material: SUS304, outer diameter: 0.55 mm, inner diameter: 0.33 mm, thickness: 0.11 mm, depth of groove 21: 0.09 mm <Bending Conditions>

Figure 9:
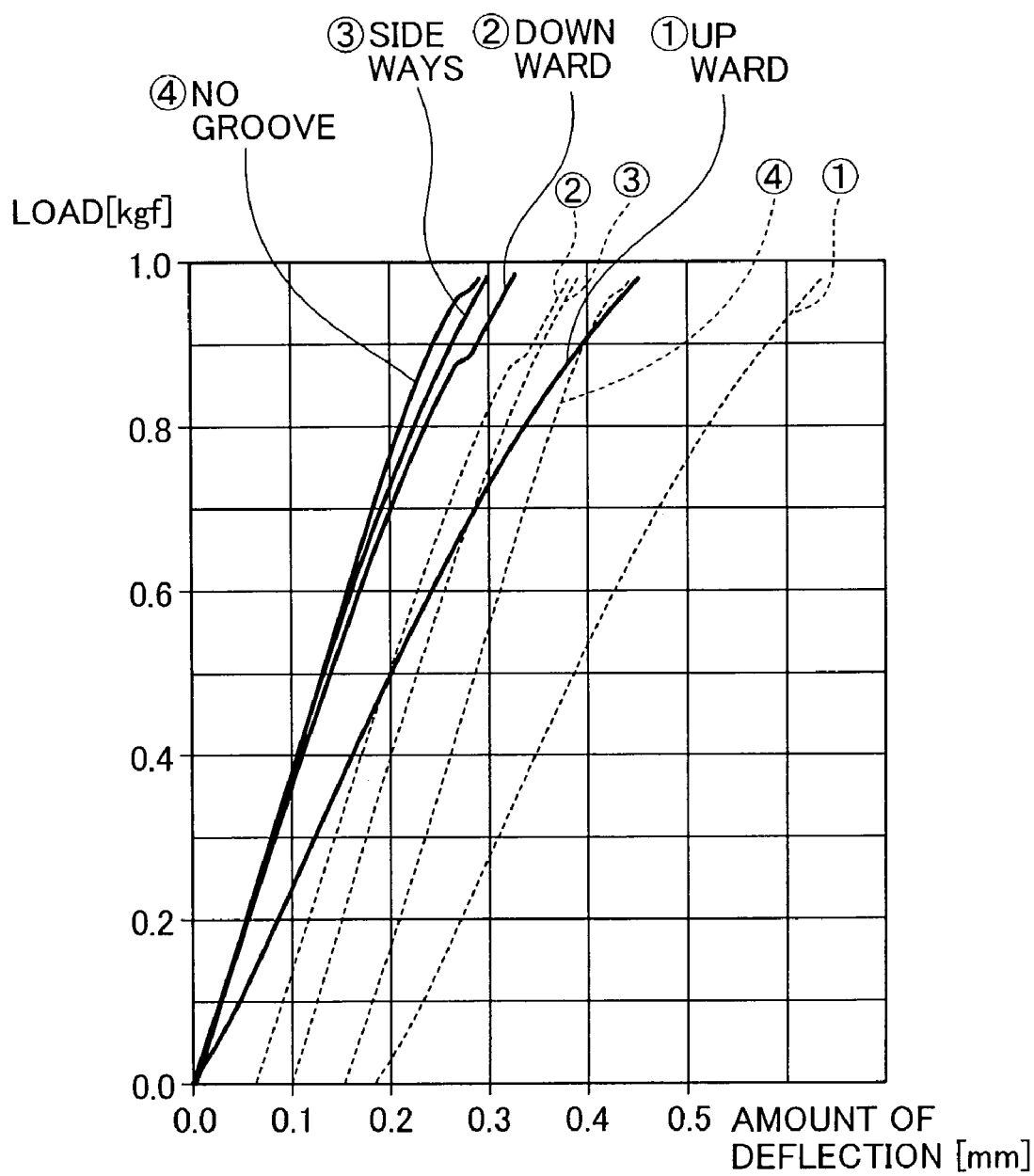
FIG. 9 is a graph showing an actual data on load and the amount of deflection in a three-point bending test of a metal tube on the vertical axis and the horizontal axis, respectively.

Fulcrum punch diameter: 5 mm, distance between fulcra: 10 mm, bending speed: 1 mm/min, maximum load: 0.98 kgf FIG. 9 is a graph in which an actual measurement data on load and the amount of deflection obtained in the above-mentioned three-point bending test are plotted on the vertical axis and the horizontal axis by a dotted line (measurement) and a solid line (after adjusting the null point). FIG. 9 shows data obtained (1) when the catheter was bent upward (state shown by A in FIG. 3), (2) when it was bent downward (state shown by B in FIG. 3), (3) when it was bent sideways (state shown by C or D in FIG. 3) and (4) when there was no groove (normal: before a groove was formed).

As understood from the results of null point-adjusted solid lines in FIG. 9, the amounts of deflection under a load of 0.98 kgf in these four cases are given below (the larger the amount of deflection, the lower the flexural rigidity becomes).
(1) Upward: 0.45 mm
(2) Downward: 0.33 mm
(3) Sideways: 0.30 mm
(4) No groove: 0.29 mm It was found from the results of this three-point bending test that flexural rigidity when the metal tube was bent upward so that the groove 21 formed portion was located on the inner side was lower than that when it was bent in other directions. It was also found that flexural rigidity when it was bent downward and sideways was almost the same as that when there was no groove.

In this embodiment, the groove 21 is formed along almost the entire length of the catheter body 2. However, in the present invention, the groove 21 may be formed in part of the catheter body 2, for example, only in the distal end side portion of the catheter body 2.

Further, the sectional form, maximum depth, width and the like of the groove 21 may be constant or may vary in the longitudinal direction of the catheter body 2.

As shown in FIG. 1, X-ray impermeable markers 5 are formed on the outer periphery of the distal end of the catheter body 2. Thus, the position of the distal end of the catheter body 2 can be confirmed by observation through a fluoroscope. In the illustrated constitution, the X-ray impermeable markers 5 are formed by winding a thin wire of gold, silver, platinum, tungsten or the like. The form of the markers is not particularly limited and may be, for example, sheet-like, band-like, C-shaped ring, or the like.

Furthermore, a layer of a hydrophilic polymer material (not shown) having lubricity in a moist state is preferably formed on the outer periphery of the catheter body 2. This reduces friction when the catheter 1 is inserted, whereby the catheter 1 can be inserted smoothly, thereby improving ease of operation and safety.

The above-mentioned catheter body 2 is used by being inserted into a guiding catheter (not shown) or contrast catheter as required when it is inserted into the blood vessel.

As shown in FIG. 1, a hub 4 is firmly fixed to the proximal end portion of the catheter body 2 liquid tightly, for instance. The lumen of the hub 4 communicates with the proximal end of the tubular lumen 23 of the catheter body 2.

The hub 4 serves as a port for inserting the guide wire 100 into the tubular lumen 23 of the catheter body 2, as a port for injecting a liquid such as a medical fluid into the tubular lumen 23, and the like. The hub 4 also serves as a grip when the catheter body 2 is operated.

The structural material of the hub 4 is not particularly limited and may be, for example, a resin material such as polyvinyl chloride, polyethylene, polypropylene, polycarbonate, polymethyl methacrylate or an acrylonitrile-styrene-butadiene copolymer, or a metal material such as stainless steel or titanium.

The guide wire 100 is a wire material having bending elasticity, and its structural material is not particularly limited and may be, for example, a plastic, pseudoelastic (super elastic) alloy (such as Ni—Ti alloy) or metal material such as stainless steel.

All or part of the surface of the guide wire 100 is preferably subjected to a treatment for providing lubricity.

The distal end portion 101 of the guide wire 100 is bent in its natural state (external force is not applied). When a blood vessel is selected, the guide wire 100 and the catheter 1 are moved forward or backward relative to each other to change the length of projection of the distal end portion 101 of the guide wire 100 from the opening at the distal end of the catheter body 2 according to the situation.

That is, making use of the curvature of the distal end portion 101 of the guide wire 100, the direction of the curvature is changed to the direction of the targeted blood vessel by rotation to insert the guide wire 100 into the targeted blood vessel. At this point, a portion projecting from the catheter body 2 of the guide wire 100 is greatly bent in most cases. The position of the groove 21 of the catheter body 2 is turned in conformity to the bent guide wire 100 so that the groove 21 is located on the depressed side (inner side) of the curvature of the guide wire 100. Accordingly, as excessive force is not applied to the curvature of the guide wire 100, the guide wire 100 is prevented from being removed from the targeted blood vessel.

Thus, in the present invention, the distal end portions of the guide wire 100 and the catheter body 2 can be bent in many ways by combining the rotation of the catheter 1 with the relative forward or backward movement of the guide wire 100 and the catheter 1. In the present invention, the use of these various bending states makes it possible to move forward the guide wire 100 and the catheter body 2 in the targeted direction smoothly and readily while flexibly coping with the complex shape of the blood vessel such as curved or branched.

A description is subsequently given of an example of usage of the catheter 1.

The guide wire 100 is inserted into the tubular lumen 23 of the catheter body 2 in advance.

Subsequently, an unshown guiding catheter or contrast catheter is percutaneously inserted close to the targeted site of the blood vessel (to be referred to as "targeted site" hereinafter) by a Seldinger method or the like using an unshown guide wire.

Next, after the above-mentioned guide wire is pulled out, the catheter body 2 of the catheter 1 of the present invention is inserted into the above-mentioned guiding catheter (contrast catheter), preceded by a new guide wire 100, until its distal end portion reaches the targeted site.

When the distal end portion of the catheter body 2 reaches the targeted site, the guide wire 100 is pulled out from the catheter body 2.

Thereafter, an injection device such as a syringe, for instance, is connected to the hub 4 to inject a contrast medium or medical fluid. Thus, the contrast medium or medical fluid is injected into the blood vessel from the distal end of the catheter body 2 through the lumen of the hub 4 and the tubular lumen 23 of the catheter body 2 in the stated order.

After the above operation has ended, the catheter body 2 is pulled out from the blood vessel together with the above-mentioned guiding catheter (contrast catheter).

Embodiment 2

Figure 4:
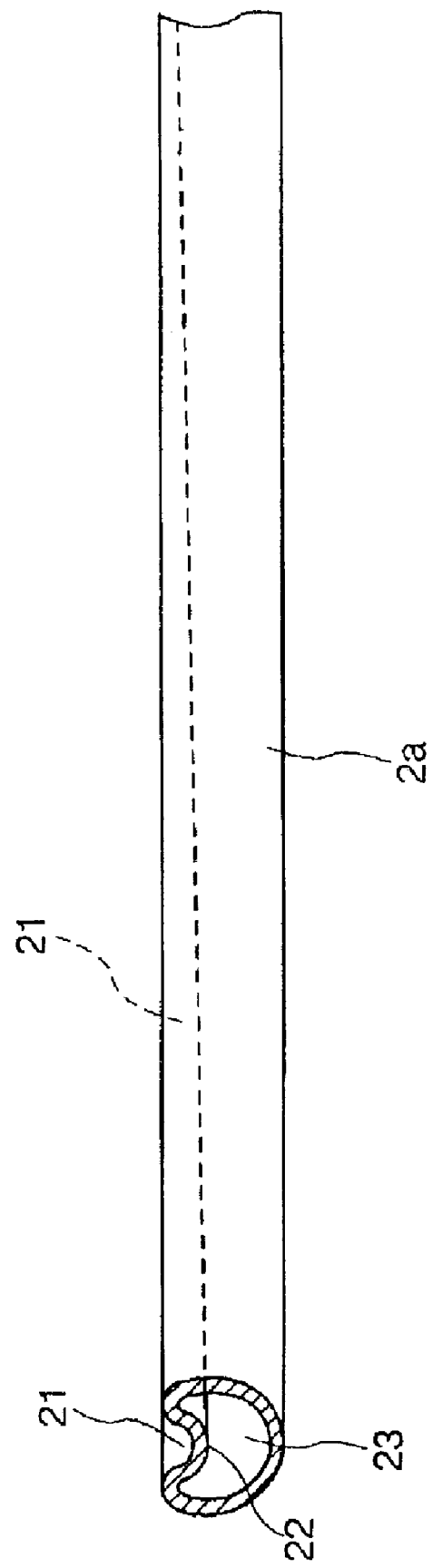
FIG. 4 is a perspective view of a catheter body in Embodiment 2 of the catheter of the present invention.

FIG. 4 is a perspective view of a catheter body according to Embodiment 2 of the catheter of the present invention. In FIG. 4, in order to make it more understandable, the length in the longitudinal direction of the catheter body 2a is shortened.

With reference to this figure, Embodiment 2 of the catheter of the present invention will be described hereinafter, focusing on the difference between the above-mentioned embodiment and this embodiment. The explanation of the same items is omitted.

This embodiment is identical to the above-mentioned Embodiment 1 except that the depth (maximum depth) of the groove 21 of the catheter body 2a decreases continuously (progressively reduces) toward the proximal end of the catheter body 2a.

In the catheter body 2a of this embodiment, the depth of the groove 21 becomes relatively larger toward the distal end and relatively smaller toward the proximal end. As a result, the catheter body 2a becomes more flexible with lower flexural rigidity toward the distal end thereof when it is bent upward so that the groove 21 formed portion is located on the inner side, and the difference in ease of bending between the direction of bending upward and other directions becomes smaller toward the proximal end thereof. Therefore, more excellent followability is obtained on the distal end side of the catheter body 2a and higher stiffness and more excellent torque transmissibility and pushability can be obtained on the proximal end side of the catheter body 2a. That is, more excellent ease of operation can be obtained in this embodiment.

The depth of the groove 21 of the catheter body 2a may be partially constant in the longitudinal direction. The depth of the groove 21 may also be null in part of the catheter body 2a. That is, there may be no groove 21 in part of the catheter body 2a.

Embodiment 3

Figure 5:
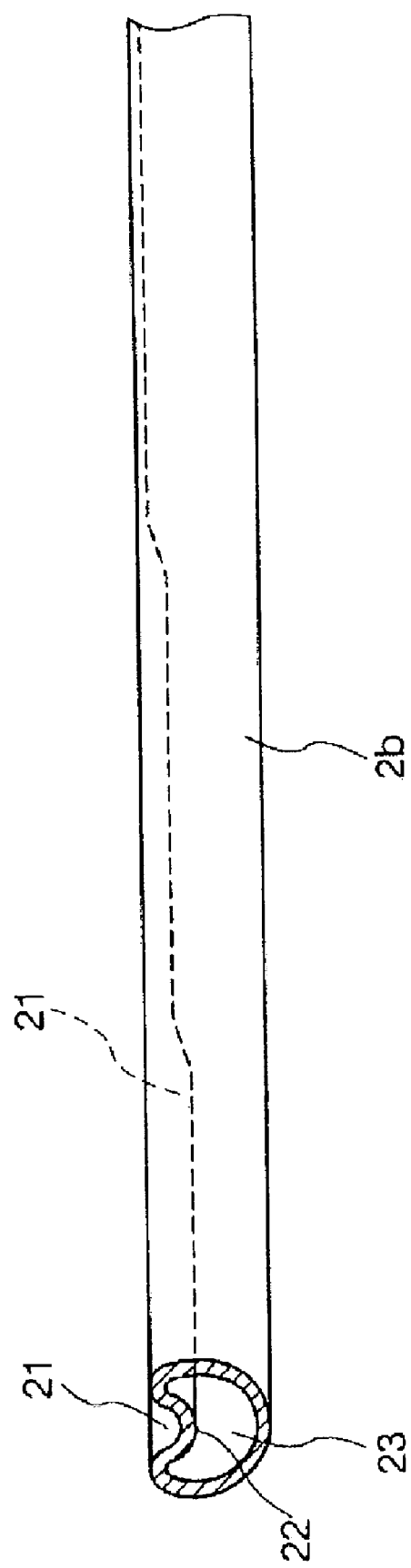
FIG. 5 is a perspective view of a catheter body in Embodiment 3 of the catheter of the present invention.

FIG. 5 is a perspective view of a catheter body according to Embodiment 3 of the catheter of the present invention. In FIG. 5, in order to make it more understandable, the length in the longitudinal direction of the catheter body 2b is shortened.

With reference to this figure, Embodiment 3 of the catheter of the present invention will be described hereinafter, focusing on the difference between the above-mentioned embodiment and this embodiment. The explanation of the same items will be omitted.

This embodiment is identical to the above-mentioned Embodiment 1 except that the depth (maximum depth) of the groove 21 in the catheter body 2b decreases stepwise (progressively reduces) toward the proximal end of the catheter body 2b.

In the catheter body 2b of this embodiment, the depth of the groove 21 decreases in plural stages (three stages in the illustrated constitution) toward the proximal end. That is, the depth of the groove 21 is relatively large on the distal end side of the catheter body 2b, relatively small on the proximal end side, and intermediate in the middle portion between them. Accordingly, the same effect as in Embodiment 2 can be obtained in this embodiment.

Further, since portions having the same depth of the groove 21 have the same flexibility, the depth and length of the groove 21 are suitably changed according to the curvature of the targeted site, thereby making it possible to easily obtain a catheter suitable for all kinds of operations.

Embodiment 4

Figure 6:
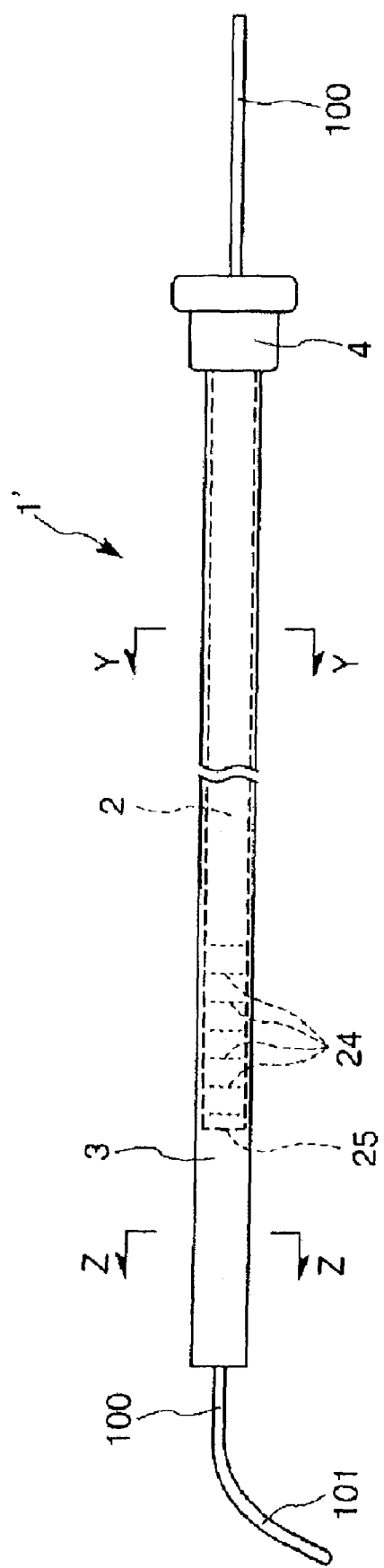
FIG. 6 is a plan view of Embodiment 4 of the catheter of the present invention.
Figure 7:
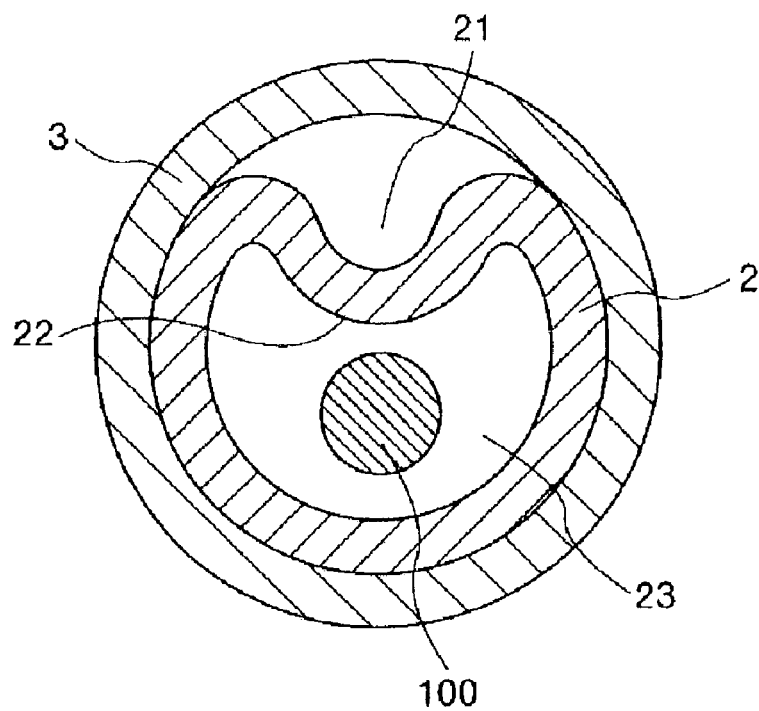
FIG. 7 is a sectional view (transverse sectional view) taken along the line Y—Y of FIG. 6.
Figure 8:
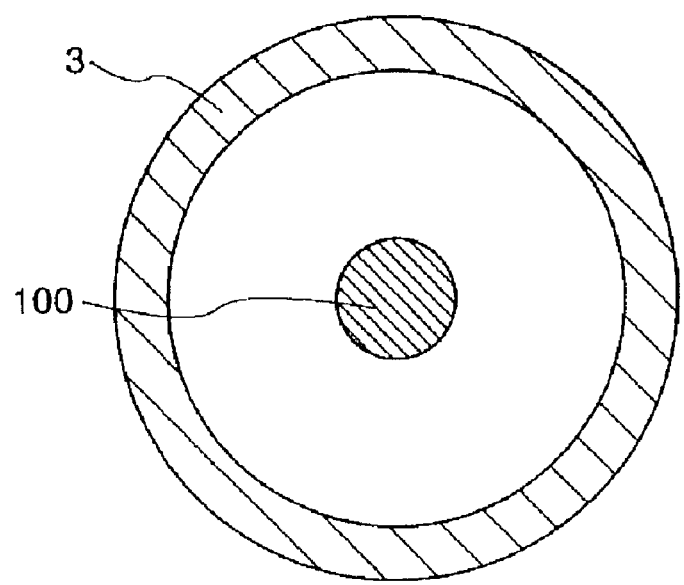
FIG. 8 is a sectional view (transverse sectional view) taken along the line Z—Z of FIG. 6.

FIG. 6 is a plan view of Embodiment 4 of the catheter of the present invention, FIG. 7 is a sectional view (transverse sectional view) taken along the line Y—Y of FIG. 6, and FIG. 8 is a sectional view (transverse sectional view) taken along the line Z—Z of FIG. 6.

With reference to these figures, Embodiment 4 of the catheter of the present invention will be described hereinafter, focusing on the difference between the above-mentioned embodiments and this embodiment. The explanation of the same items will be omitted.

This embodiment is identical to the above-mentioned Embodiment 1 except that it has a tubular member 3 for covering the outer periphery of the catheter body 2 and that plural slits 24 are formed in the tubular wall of the distal end portion of the catheter body 2.

As shown in FIG. 6 and FIG. 7, the tubular (cylindrical) member 3 for covering the outer periphery of the catheter 1' of this embodiment is formed along the entire length of the catheter body 2.

The tubular member 3 is made from a synthetic resin material and has flexibility. Examples of the synthetic resin material constituting the tubular member 3 include: polyolefins such as polypropylene, polyethylene and an ethylene-vinyl acetate copolymer; polyesters such as polyethylene terephthalate (PET) and polybutylene terephthalate (PBT); fluorine-based resins such as polytetrafluoroethylene and an ethylene-tetrafluoroethylene copolymer; resins having flexibility such as polystyrene-based resin, polyamide, polyurethane and polyimide; polyamide elastomer, polyester elastomer, polyurethane elastomer, polystyrene elastomer and fluorine-based elastomer, or a combination of two or more out of these (such as a laminate consisting of plural layers and polymer blends thereof). Since the tubular member 3 is made from a soft material having higher flexibility than the catheter body 2, the resistance of the tubular member 3 can be substantially ignored when the catheter body 2 is bent.

In this embodiment, as the outer periphery of the catheter body 2 is covered with the tubular member 3 having such flexibility, a stimulus to the inner wall of the blood vessel can be further reduced, thereby increasing safety.

Further, in the catheter 1', the tubular member 3 extends farther than the distal end 25 of the catheter body 2 in the forward end direction. That is, as shown in FIG. 8, the distal end portion of the catheter 1' is devoid of the catheter body 2 and composed only of the tubular member 3. Thus, the distal end portion of the catheter 1' has higher flexibility and can further reduce a stimulus to the inner wall of the blood vessel, thereby making it possible to obtain higher safety. Followability can also be further improved. The length of a portion devoid of the catheter body 2 of the distal end portion is not limited but is preferably 2 to 300 mm.

The outer periphery of the tubular member 3 is preferably covered with a lubricant layer (not shown) of a hydrophilic (or water-soluble) polymer material. Thus, when the outer periphery of the tubular member 3 contacts blood, physiological saline, or the like, the friction coefficient decreases and lubricity is provided, thereby further enhancing the slidability of the catheter 1', resulting in further improved torque transmissibility, pushability and safety.

The tubular member 3 is not limited to the one covering the total length of the catheter body 2 but may be the one covering at least part of the outer periphery of distal end side of the catheter body 2. In this case, the same effect as above can be obtained.

Further, as shown in FIG. 6, in this embodiment, plural slits 24 are formed in the tubular wall of a predetermined range on the distal end side of the catheter body 2. In the illustrated constitution, the slits 24 extend in a direction substantially perpendicular to the longitudinal direction of the catheter body 2 and are arranged almost parallel to one another at predetermined intervals. At the slit 24 formed sites, the flexibility of the catheter body 2 becomes high, whereby the catheter 1' can obtain higher followability.

The provision of the tubular member 3 prevents the contrast medium or medical fluid injected into the tubular lumen 23 from leaking from the slits 24.

Further, spiral slits may be formed in the tubular wall of the distal end side portion of the catheter body 2 in place of the plural slits 24. The same effect as above can be obtained in this way as well. In this case, these spiral slits are preferably formed in such a manner that the spiral pitch (interval) between the spiral slits becomes smaller continuously or stepwise toward the distal end. Thus, the distal end side portion of the spiral slit formed portion can be made more flexible.

Furthermore, the slits may be formed in such a manner that they extend in the longitudinal direction of the catheter body 2.

Embodiment 5

Figure 10:
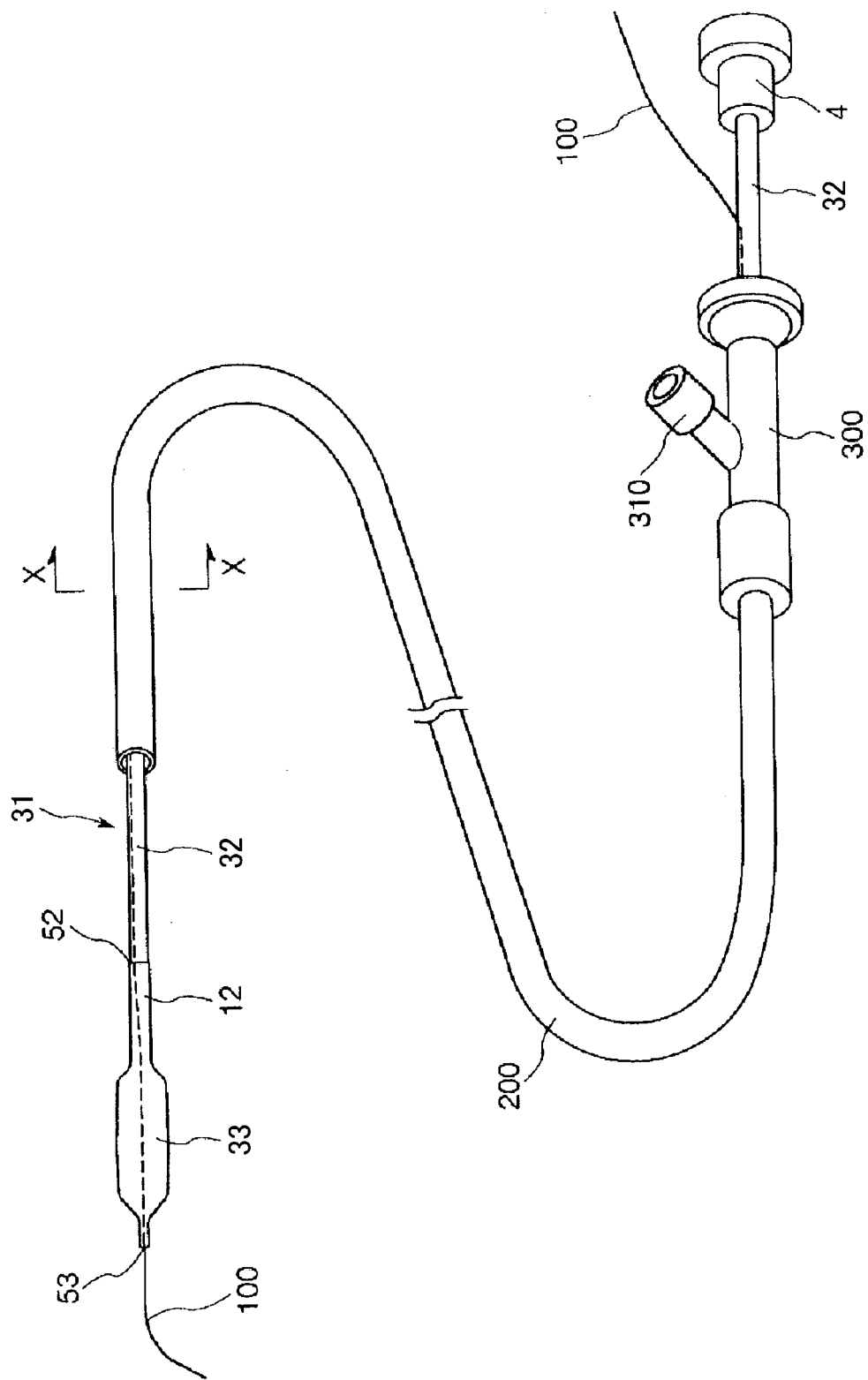
FIG. 10 is a perspective view showing a balloon catheter of Embodiment 5 of the present invention inserted in a lumen of a guiding catheter.
Figure 11:
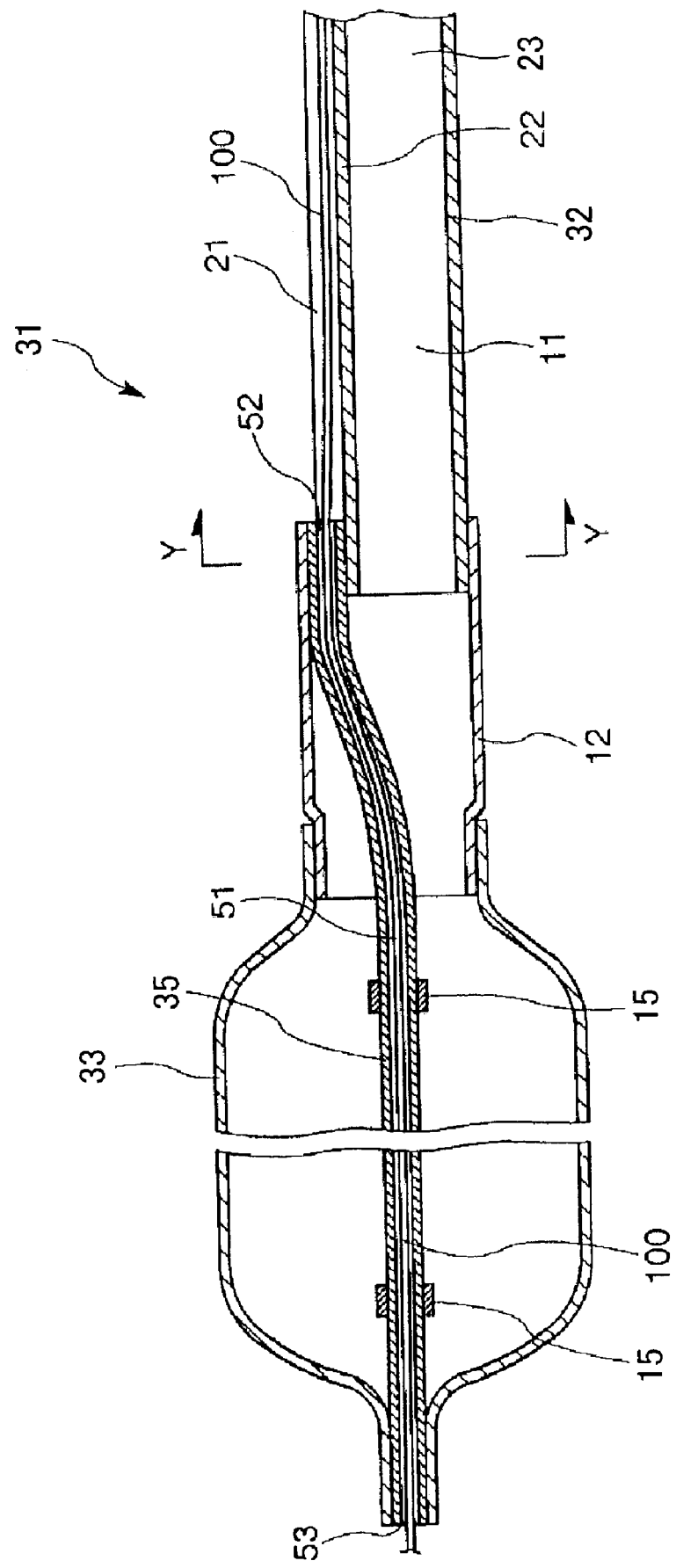
FIG. 11 is a longitudinal sectional view of the distal end portion of the catheter shown in FIG. 10.
Figure 12:
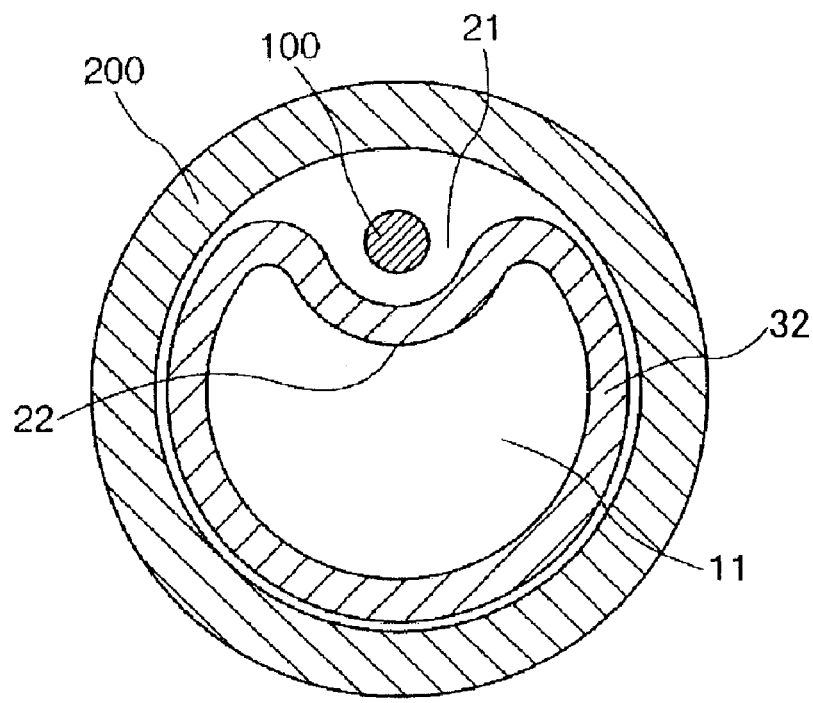
FIG. 12 is a sectional view (transverse sectional view) taken along the line X—X of FIG. 10.
Figure 13:
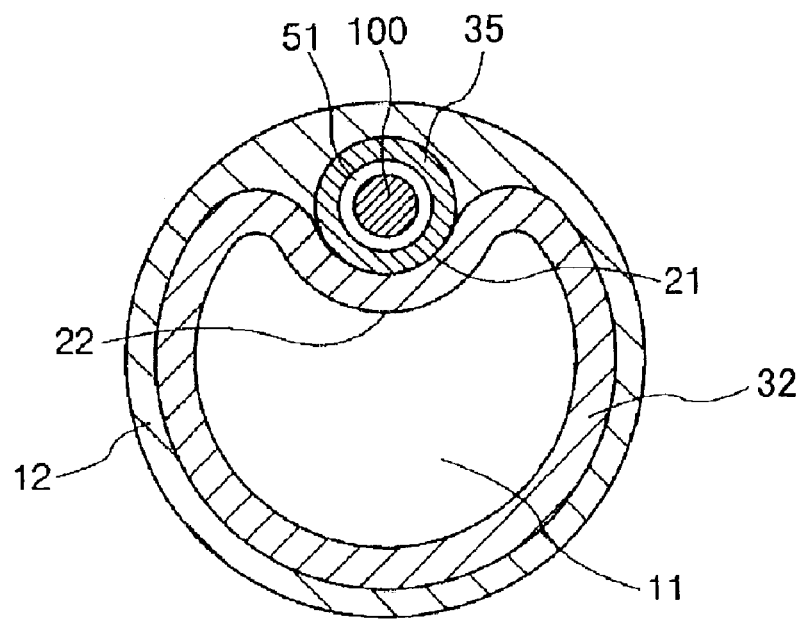
FIG. 13 is a sectional view (transverse sectional view) taken along the line Y—Y of FIG. 11.

FIG. 10 is a perspective view showing a balloon catheter (to be simply referred to as "catheter" hereinafter) of Embodiment 5 of the present invention inserted in a lumen of a guiding catheter, FIG. 11 is a longitudinal sectional view of the distal end portion of the catheter shown in FIG. 10, FIG. 12 is a sectional view (transverse sectional view) taken along the line X—X of FIG. 10, and FIG. 13 is a sectional view (transverse sectional view) taken along the line Y—Y of FIG. 11. The perspective view of a catheter body of the catheter shown in FIG. 10 is shown in FIG. 3.

The catheter 31 shown in FIG. 10 is a rapid-exchange type balloon catheter which includes a catheter body 32 having flexural elasticity, an inflatable and deflatable balloon (expandable body) 33 which is mounted on the distal end side of the catheter body 32, and a hub 4 mounted on the proximal end side of the catheter body 32. The constitution of each part will be described hereinbelow.

The catheter body 32 is made from a metal material and is tubular. Thus, the catheter body 32 has higher rigidity (flexural rigidity and torsional rigidity) than a catheter body made from a synthetic resin material (plastic). Therefore, the catheter body 32 has high stiffness even when its outer diameter is relatively small. As a result, the catheter 31 has excellent torque transmissibility so that torque applied from the proximal end side is transmitted to the distal end side without fail and excellent pushability so that an operator's push-in force for advancing the catheter in the blood vessel can be transmitted from the proximal end side to the distal end side without fail.

That is, the catheter 31 of the present invention obtains excellent ease of operation even when the outer diameter of the catheter body 32 is relatively small and is therefore particularly suitable for use as a catheter having a relatively small diameter which can be inserted into a relatively narrow blood vessel. Thus, the outer diameter (average outer diameter) of the catheter body 32 is not particularly limited but is preferably about 0.2 to 3 mm, and more preferably about 0.3 to 2 mm. The outer and inner diameters of the catheter body 32 may change in the longitudinal direction.

Further, the length of the catheter body 32 is not particularly limited and suitably determined according to the site of using the catheter 31 and a case of a disease. In general, it is preferably about 100 to 200 cm.

As shown in FIG. 11, the lumen 23 of the catheter body 32 constitutes a balloon lumen 11 which communicates with the inside of a balloon 33 to be described below. The balloon lumen 11 serves as a passage for supplying a working fluid for inflating and deflating the balloon 33 into the inside space of the balloon 33.

In the present invention, the provision of the groove 21 contributes to the reduction of the diameter of the guiding catheter 200. That is, since the guide wire 100 is received in the groove 21 in the catheter 31 as shown in FIG. 12, there is no need to form a space for inserting the guide wire 100 between the outer periphery of the catheter body 32 and the inner periphery of the guiding catheter 200, whereby the guiding catheter 200 may have almost the same small inner diameter as the outer diameter of the catheter body 32. Accordingly, the guiding catheter 200 and the catheter 31 can be inserted (introduced) into a narrower blood vessel.

Further, since the guide wire 100 is received in the groove 21, the movement in the transverse direction of the guide wire 100 with respect to the catheter 31 is fixed and a play can be eliminated. Since the guide wire 100 thus displaces together with the catheter 31 at the time of operating the catheter 31, the above-mentioned torque transmissibility and pushability become more excellent.

Furthermore, this groove 21 also serves as a guide passage for moving the guide wire 100 therealong.

In this embodiment, the groove 21 is formed along almost the entire length of the catheter body 32. In the present invention, the groove 21 may be formed only in the distal end side portion of the catheter body 32.

The sectional form, maximum depth, width and the like of the groove 21 may be constant or may vary in the longitudinal direction of the catheter body 32.

As shown in FIG. 11, the balloon 33 is composed of a cylindrical film member and connected (fixed) to the distal end portion of the catheter body 32 by a cylindrical connection member 12. The balloon lumen 11 communicates with the inside of the balloon 33 through the lumen of the connection member 12 from the lumen of the catheter body 32.

The proximal end portion of the balloon 33 is sealed to the outer periphery of the distal end portion of the connection member 12 air tightly or liquid tightly. The distal end portion of the balloon 33 is sealed to the outer periphery of the distal end portion of the inner tube 35 to be described below air tightly or liquid tightly. The sealing of these portions is carried out by fusion bonding or bonding with an adhesive, for example.

The balloon 33 is shriveled and folded before it is inflated (deflated). It is inflated when a working fluid is supplied into the inside of the balloon 33 (state shown in FIG. 10 and FIG. 11).

The structural material of the balloon 33 is a polymer material (particularly, a thermoplastic resin). In this case, the balloon 33 has flexibility as a whole but it is preferably made from a material having relatively low elasticity (elongation).

Examples of the structural material of the balloon 33 include polyester resins such as polyethylene terephthalate and polybutylene terephthalate; olefin-based resins such as polyester elastomer, polyethylene and polypropylene; or those obtained by crosslinking these resins (particularly, crosslinking by exposure to an electron beam); vinyl chloride resin; polyamide-based resins such as nylon 11, nylon 12 and nylon 610; polyamide elastomer; polyurethane resin; an ethylene-vinyl acetate copolymer; or those obtained by crosslinking these polymers; or polymer blends and polymer alloys containing at least one of these.

Further, the balloon 33 may be composed of a laminate consisting of plural films of these materials. In this case, the laminate can be obtained by co-extrusion molding of layers or assembling layers together by adhesion bonding, fusion bonding, or the like, or forming one layer on another layer by coating, for instance. A soft resin layer, layer of a lubricant material, layer of an antithrombic material, or the like may also be formed on the external side or internal side of a layer composed of one of the above-mentioned materials.

The structural material of the balloon 33 may contain, for example, an antithrombic material such as heparin, prostaglandin, uroxinase or an arginine derivative.

The tubular inner tube 35 is arranged and inserted into the inside (inner side) of the balloon 33 and the connection member 12. A guide wire lumen 51 for inserting the guide wire 100 is formed in the lumen of the inner tube 35.

The distal end portion of the guide wire lumen 51 (inner tube 35) is open on the distal end side (distal end portion) of the balloon 33 and the proximal end portion of the guide wire lumen 51 (inner tube 35) is open near a bonding portion between the catheter body 32 and the connection member 12. That is, the guide wire lumen 51 communicates with the distal end side and the proximal end side of the balloon 33.

The guide wire 100 is inserted into the guide wire lumen 51, the distal end side of the guide wire 100 projects from the opening 53 at the distal end of the guide wire lumen 51, and the proximal end side of the guide wire 100 is exposed to the outside of the catheter 31 through the opening 52 at the proximal end of the guide wire lumen 51 and is situated in the groove 21 almost parallel to the catheter body 32.

X-ray impermeable markers 15 showing the boundaries between the cylindrical portion and the conical portions of the balloon 33 when the balloon 33 is inflated are formed on the outer periphery of the inner tube 35. The X-ray impermeable markers 15 are made of, for example, a thin (having a small diameter) wire, band, or the like of gold, silver, platinum, tungsten, etc.

Further, as shown in FIG. 13, the proximal end portion of the inner tube 35 is inserted into the distal end portion of the groove 21, and the inner periphery of the proximal end portion of the connection member 12 is sealed to the proximal end portion of the inner tube 35 and the outer periphery of the distal end portion of the catheter body 32 air tightly or liquid tightly. Due to this constitution, the opening 52 at the proximal end of the guide wire lumen 51 is formed continuous to the distal end portion of the groove 21. As shown in FIG. 11, since the guide wire 100 extends linearly in the groove 21 from the guide wire lumen 51, it has low resistance to sliding with the catheter 31, thereby making it possible to carry out the operation of moving forward or backward the catheter 31 and the guide wire 100 relative to each other smoothly.

The length of the guide wire lumen 51 is not particularly limited but is preferably about 3 to 30 cm, more preferably about 7 to 20 cm in consideration of the operation of exchanging the catheter.

The structural materials of the connection member 12 and the inner tube 35 are not particularly limited but preferably a polymer material having flexibility includes, for example, a polyolefin such as polyethylene, polypropylene, an ethylene-propylene copolymer, an ethylene-vinyl acetate copolymer or a crosslinked ethylene-vinyl acetate copolymer; thermoplastic or thermosetting resin such as polyester, polyvinyl chloride, polyurethane, polyamide, polyimide, polyamide elastomer, polyurethane elastomer, polyester elastomer, polyfluororesin, or other.

As shown in FIG. 10, the hub 4 is mounted to the proximal end portion of the catheter body 32. The lumen of the hub 4 communicates with the proximal end of the balloon lumen 11. A balloon inflating device (not shown) such as a syringe is connected to the hub 4 in order to supply a working fluid supplied therefrom into the inside of the balloon 33 through the balloon lumen 11 or extract the working fluid, thereby inflating or deflating the balloon 33.

The working fluid for inflating the balloon is liquid because it has an advantage that the volume of a liquid does not change even when pressure is applied to the liquid whereas the volume of a gas decreases when pressure is applied to the gas. In addition, the liquid is used from the viewpoints of reduction of a pressure loss and safety if, by any chance, the balloon ruptures. A liquid having X-ray contrast properties is preferred as the liquid. For example, a liquid prepared by diluting an X-ray contrast medium such as a contrast medium for the artery with physiological saline to several folds may be used.

Preferably, all or part of the surface of the guide wire 100 is subjected to a treatment for providing lubricity, the distal end portion thereof is tapered corresponding to characteristic properties such as butt resistance and bend resistance, and the outer diameter thereof progressively decreases toward the distal end. Accordingly, when the guide wire 100 is inserted into the blood vessel from the distal end side thereof to reach the targeted site (the coronary artery, etc.), the insertion of the guide wire 100 can be performed smoothly and the insertion operation can be performed easily and safely while flexibly coping with the complex shape such as curvature or branching of the blood vessel.

The above catheter 31 and the guide wire 100 are inserted into the guiding catheter 200 before use. As shown in FIG. 12, the guiding catheter 200 is a tubular member having flexibility and an inner diameter larger than the outer diameter of the catheter body 32. The structural material of the guiding catheter 200 is not particularly limited but may be the same as the structural material of the connection member 12 and the inner tube 35, for example.

As shown in FIG. 10, a Y connector 300 is mounted on the proximal end side of the guiding catheter 200. A lumen is formed inside of the Y connector 300 in the longitudinal direction and this lumen communicates with the lumen of the guiding catheter 200. The catheter 31 and the guide wire 100 project from the proximal end of the Y connector 300 through the lumens of the guiding catheter 200 and the Y connector 300.

Further, a tubular branched portion 310 is formed on the Y connector 300. This branched portion 310 is used, for example, to inject an X-ray contrast medium into a desired targeted site in the blood vessel. The X-ray contrast medium injected from the branched portion 310 is discharged from the opening at the distal end of the guiding catheter 200 through the lumen of the Y connector 300 and the lumen of the guiding catheter 200.

The catheter of the present invention has been described above with reference to the illustrated embodiments. However, the present invention is not limited to these and components constituting the catheter may be substituted by any arbitrary known components which can exhibit the same functions. Any arbitrary known component may also be added.

A description is subsequently given on usage when the catheter 31 is applied to PTCA.

[1] According to the Seldinger method, a catheter introducer is stuck into a femoral artery (or brachial artery), and the guiding catheter 200 containing a guide wire (not shown) is inserted into the artery from the sheath of the catheter introducer, moved forward or backward or turned repeatedly while the guide wire precedes the guiding catheter 200 until the distal end portion thereof reaches the inlet of the coronary artery and is left there.

[2] After the above-mentioned guide wire is pulled out, the catheter 31 having the guide wire 100 situated in the groove 21 and the guide wire lumen 51 is inserted from a hemostatic valve provided in the opening at the proximal end of the Y connector 300 and moved forward along the lumen of the guiding catheter 200 toward the distal end direction, preceded by the guide wire 100, and the distal end portion of the catheter 31 is projected from the opening at the distal end of the guiding catheter 200. In the present invention, as described above, the catheter 31 can be advanced smoothly and quickly while it is turned as required in accordance with the curvature of the guiding catheter 200 and the curvature of the blood vessel.

[3] When the distal end of the catheter 31 reaches the coronary artery, the guide wire 100 is moved forward while it is turned as required so that the distal end thereof passes through the stricture of the coronary artery which is the targeted site. In the present invention, since the guide wire 100 is received in the groove 21, it is also turned by the rotation of the catheter 31 described above and is not twined around the outer periphery of the catheter body 2, thereby improving the operation ease of the guide wire 100. Therefore, the work of passing the guide wire 100 through the stricture of the coronary artery can be carried out readily and reliably.

During this, the X-ray contrast medium is injected from the branched portion 310 of the Y connector 300 to be supplied into the coronary artery through the lumens of the Y connector 300 and the guiding catheter 200 to create an image for confirming the position.

[4] When the distal end of the guide wire 100 has passed through the stricture of the coronary artery, the advancement of the guide wire 100 is stopped and then the catheter 31 is advanced along the guide wire 100 slowly to position the balloon 33 in the stricture of the coronary artery using the X-ray impermeable markers 15 as a clue.

Then, the working fluid is injected from the hub 4 to be supplied into the balloon 33 through the lumen of the hub 4 and the balloon lumen 11 to inflate the balloon 33 at 4 to 18 atm, which differs according to the size of the balloon 33. Thus, the stricture of the coronary artery is expanded.

[5] To further expand the stricture of the coronary artery from this state, for example, the inserted catheter is exchanged with a catheter suitable therefor that has a larger balloon.

To exchange the catheter 31 inserted into the coronary artery with a new catheter, the balloon 33 is deflated while the guide wire 100 and the guiding catheter 200 are left as they are and then the hub 4 is pulled toward the proximal end to retreat the catheter 31 and pull it out. Since the proximal end of the guide wire 100 is fixed by the finger or the like, the catheter 31 can be pulled out while the guide wire 100 is left in the body.

The proximal end of the guide wire 100 is inserted into a hole at the distal end of the new catheter to be exchanged (balloon catheter, etc.), and the catheter is moved forward along the guide wire 100 to reach the targeted site through the Y connector 300 and the lumen of the guiding catheter 200 in the same manner as described above. As a result, exchange of the catheter is completed. Thereafter, operation is carried out according to the purpose of the exchanged catheter.

The balloon catheter of the present invention has been described above with reference to the illustrated embodiments. However, the present invention is not limited to these and components constituting the balloon catheter may be substituted by any arbitrary known components which can exhibit the same functions. Any arbitrary known components may also be added.

EFFECT OF THE INVENTION

As described above, according to the present invention, there is obtained a catheter which has a simple structure, excellent torque transmissibility, pushability and followability and allows extremely high ease of operation.

Further, when the catheter body has a portion where the depth of the groove decreases continuously or stepwise toward the proximal end thereof, torque transmissibility, pushability and followability can be further improved.

Further, when the groove of the catheter body is formed by plastically transforming the tubular wall of the catheter body, the catheter can be produced easily and the above-mentioned effect can be obtained at lower production cost.

Further, when there is provided a tubular member for covering the outer periphery of at least the distal end side portion of the catheter body, which is made from a synthetic resin material, higher safety is obtained.

Further, when at least part of the guide wire can be inserted into the groove of the catheter body, the guide wire can be used in combination with a guiding catheter having a smaller diameter and can be inserted into a narrower blood vessel.

Furthermore, when the groove of the catheter body is formed by plastically transforming the tubular wall of the catheter body, the catheter can be produced easily and the above-mentioned effect can be obtained at lower production cost.

What is claimed is:

1. A rapid exchange balloon catheter comprising:
a tubular catheter body made from a metal material and possessing a length of 100–200 cm;
a balloon which can be inflated and deflated and is mounted on the distal end side of the catheter body;
a balloon lumen which is formed of a lumen of the catheter body and that communicates with the inside of the balloon, an inner tube is inserted into the balloon and a guide wire lumen is formed of the lumen of the inner tube;
the guide wire lumen possessing a first opening at a distal end side of the balloon and a second opening at a proximal end side of the balloon, with said second opening positioned 3–30 cm from said first opening, and said guide wire lumen being adapted to receive a guide wire inserted from the distal end side of the balloon to the proximal end side outside of the catheter body, and
the catheter body has a groove formed in a longitudinal direction in the outer periphery thereof in such a manner that a tubular wall of the catheter body is caved in, the groove extending along almost the entire length of the catheter body, and when the catheter body is bent in one direction into a bent configuration with the groove located on an inner side of the bent configuration, the groove causes flexural rigidity of the catheter body to be lower than if the catheter body is bent in other directions; and
the thickness of the tubular wall of the catheter body is almost constant along the entire circumference including the groove formed portion,
wherein a guide wire is insertable to the guide wire lumen from the distal end side of the balloon, is exposed from the proximal end side of the balloon outside of the catheter body, and is positionable in said groove substantially parallel to the catheter body.

* * * * *

UNITED STATES PATENT AND TRADEMARK OFFICE
CERTIFICATE OF CORRECTION

PATENT NO. : 7,163,524 B2  Page 1 of 1
APPLICATION NO. : 10/368432
DATED : January 16, 2007
INVENTOR(S) : Ishii Tatsuzo It is certified that error appears in the above-identified patent and that said Letters Patent is hereby corrected as shown below:

Column 5, Line 55: change "mile" to --male--.

Signed and Sealed this

Eighteenth Day of August, 2009

David J. Kappos
*Director of the United States Patent and Trademark Office*